United States Patent [19]

Krasner

[11] 4,306,567

[45] Dec. 22, 1981

[54] DETECTION AND MONITORING DEVICE

[76] Inventor: Jerome L. Krasner, 14 Swallow Dr., Newton, Mass. 02162

[21] Appl. No.: 115,403

[22] Filed: Jan. 25, 1980

Related U.S. Application Data

[63] Continuation of Ser. No. 864,279, Dec. 22, 1977, abandoned.

[51] Int. Cl.³ .............................................. A61B 5/08
[52] U.S. Cl. .................................. 128/671; 128/689; 128/721
[58] Field of Search ................................ 128/670–671, 128/691–694, 661–663, 715, 721–724

[56] References Cited

U.S. PATENT DOCUMENTS

| | | | |
|---|---|---|---|
| 2,848,992 | 8/1958 | Pigeon | 128/706 |
| 3,140,710 | 7/1964 | Glassner et al. | 128/700 |
| 3,171,406 | 3/1965 | Baum et al. | 128/715 |
| 3,426,151 | 2/1969 | Tygart | 128/904 X |
| 3,513,832 | 5/1970 | Klemm et al. | 128/671 |
| 3,532,086 | 10/1970 | Underwood | 128/668 |
| 3,572,317 | 3/1971 | Wade | 128/671 |
| 3,587,562 | 6/1971 | Williams | 128/696 |
| 3,643,652 | 2/1972 | Beltran | 128/725 |
| 3,811,428 | 5/1974 | Van Horn et al. | 128/698 |
| 4,000,461 | 12/1976 | Barber et al. | 128/708 |
| 4,088,138 | 5/1978 | Diack et al. | 128/419 D |

FOREIGN PATENT DOCUMENTS 1268644 3/1972 United Kingdom .

OTHER PUBLICATIONS

Beerwinkle, K. R. et al., "A Low-Power Combination ECG-Resp. Tel. Transmitter", IEEE Biomed. Engrg. Trans., vol. BME-23, No. 6, pp. 484–486, Nov. 1976.
Grassi, C. et al., "Normal & Pathological Respiratory Sounds Analyzed by Means of A New Phonopneumographic Appar.", Respiration 33:315-324, (1976).

*Primary Examiner*—Robert W. Michell
*Assistant Examiner*—Francis J. Jaworski
*Attorney, Agent, or Firm*—Schiller & Pandiscio

[57] ABSTRACT

One or more physiological rhythmic functions can be monitored by detecting pressure waves within a predetermined, relatively narrow, frequency band associated with each of said functions, generating a corresponding signal representative of said pressure waves associated with each of said functions and demodulating the signal to detect any amplitude modulation frequency related to the rhythmic rate of each of said functions.

26 Claims, 5 Drawing Figures

DETECTION AND MONITORING DEVICE

The Government may have a paid-up license in this invention and the right in limited circumstances to require the patent owner to license others on reasonable terms.

COPENDING APPLICATION

This application is a continuation application of U.S. Ser. No. 864,279 filed Dec. 22, 1977, now abandoned.

This invention relates generally to the acquisition of certain physiological signals and more particularly to respiration and heart rate detection and monitoring.

It is frequently desirable to detect and monitor certain rhythmic physiological or bodily functions, such as respiration and heart rate, particularly when the monitored body is a new born infant or someone infirmed. For example, approximately 54,000 infants now die annually as a result of crib death or sudden infant death syndrome (SIDS). Since apnea, or the cessation of breathing is associated with SIDS, various devices, known known as apnea monitors, are now currently being used to monitor and detect apnea in perinatal patients in the belief that detecting respiratory cessation and immediately giving aid, at least some of these deaths might be avoided.

Current, commercially available apnea monitors can be divided generally into two groups, i.e., those directly contacting the body and those considered to be non contacting. Among the contacting type, one available monitor utilizes a strain gage sensor placed around the thorax so as to measure chest expansion. Frequently, however, infants exhibit greater abdominal breathing and less thoracic breathing so that the breathing may go undetected. Further, the device is very motion artifact sensitive. Another popular contacting technique is one employing an impedance pneumograph in which a 50 KHz AC signal is created between thoracically-mounted electrodes and changes in chest impedance are detected. This latter technique makes use of the corelation between the measured impedance and respiratory tidal volume in the non-moving subject, whereby changes in subject position effect the amplitude of the detected signals. It has been found, however, that certain movements which can occur in a non-breathing subject can produce signals which look very similar to respiratory wave forms. Another device called the magnetometer detects the distance between two electrodes, one placed on the chest and the other on the back. Although respiration can be detected in this manner, the device is extremely sensitive to motion artifacts. Other types of contacting monitors includes those employing thermistors adapted to be placed in nasal orifices. These latter devices however are limited by associated problems such as nasal obstruction, mouth breathing and mucus adhesion to the sensor.

Among the noncontacting types of commercially-available monitors are those employing air mattresses. One, for example, comprises a plurality of air chambers or segments in fluid communication with one another and means for detecting air exchange between adjacent matress segments which occurs from motion with respiration of a body lying on the mattress. Another type of air mattress monitoring device includes capacitive plates to that motion associated with respiration changes the capacitive reactance between the plates, which in turn is detected by a bridge circuit. Another type of noncontacting monitor employs an ultrasonic sensor to detect motion via phase change. All of the noncontacting monitors described are, of course, motion sensitive and thus sensitive not only to the motion associated with respiration but also motion artifacts as well. For example, body movements which may be confused with respiration in these as well as other systems include normal body motions associated with active sleep states and awake activity, violent motions associated with a struggle to breathe, and thoracic movements associated with normal breathing in which air is exchanged between abdominal pulmonary lobes and thoracic lobes (laryngeal or upper airway apnea). Thus, apnea may go undetected for a sufficient but critical period of time.

It is a general object of the present invention to overcome or at least minimize the problems of the prior art.

More specifically, it is an object of the present invention to provide an improved respiratory monitoring device which is substantially insensitive to motion and, in particular, relatively insensitive to motion artifacts.

Another object of the present invention is to provide an improved respiratory monitor which is relatively simple to attach to the monitored body and yet provides for comfort and reliability in monitoring respiration.

I have empirically determined that, generally speaking many physiological rhythmic functions, generate sonic signals within a relatively narrow band of frequencies. For example, during normal respiration a healthy person will generate acoustical signals at a maximum signal-to-noise ratio within a relatively narrow bandwidth of frequencies when air passes through the trachea even though the respiration rate may vary. Specifically, the acoustic signals are believed to be created by the sonic pressures created by the non-laminar or uneven flow of air in the trachea as it expands and pulls downward during the inflation of the lungs. Similar studies have shown that acoustical signals associated with normal cardiac contractions, i.e., heart rate, are also within a relatively narrow bandwidth of frequencies.

It is therefore another object of the present invention to provide a system for and method of detecting the pressure waves associated with one or more physiological rhythmic functions.

Still another object of the present invention, is to monitor respiration by detecting the flow of air through the trachea.

Yet another object of the present invention is to provide an improved respiratory monitor which can easily be adapted to also simultaneously monitor heart rate with the same sensor.

And another object of the present invention is to provide an improved respiration monitor which detects the flow of air through the trachea and which can easily be adapted for use with respiratory instruments, such as endotracheal and tracheostomy tubes.

These and other objects are achieved by an improved apparatus for monitoring one or more physiological rhythmic functions comprising means for detecting pressure moves within a predetermined, relatively narrow, frequency band characteristic of each of said functions, means for generating a signal representative of the detected waves associated with each function and means for determining the amplitude modulation frequency of each of said signals as a function of the rate of said function.

Other objects of the invention will in part be obvious and will in part appear hereinafter. The invention accordingly comprises processes involving the several steps with respect to the others, and the apparatus possessing the construction, combination of elements, and arrangement of parts which are exemplified in the following detailed disclosure and the scope of the application of which will be indicated in the claims.

For a further understanding of the nature and objects of the present invention, reference should be had to the following detailed description taken in connection with the accompany drawings wherein.

In the drawings the same numerals refer to like parts.

Figure 1:
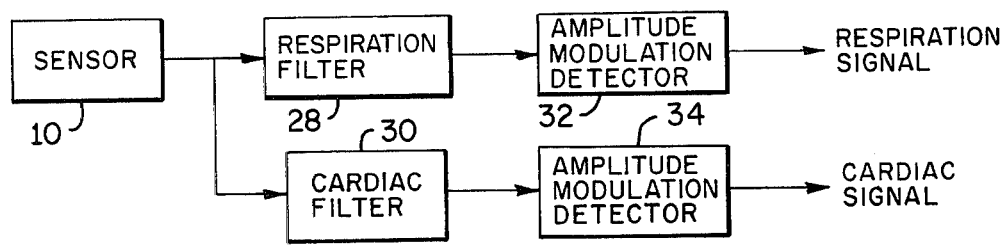
FIG. 1 is a block diagram generally showing the preferred embodiment of the present invention.

The present invention relates to the acquisition of certain physiological rhythmic signals by detecting the sonic pressure waves associated with each of the physiological rhythmic functions. More specifically, an embodiment of the present invention as shown in FIG. 1 is a device for acquiring respiration and/or heart rate signals which are initially sensed by sensing means 10 for detecting the pressure waves associated with the particular physiological function. Sensing means 10 preferably includes a pressure sensor, such as a microphone, sensitive to acoustical energy, in the bandwidths of interest, although it will be appreciated that other types of sensors can be used such as those comprising piezoelectric devices.

More spcifically, I have empirically determined that the sonic pressures created by the non-laminar flow of air in the trachea as it expands and pulls downward during inflation of the lungs generates acoustical signals a maximum signal-to-noise ratio typically within a frequency bandwidth between about 300–600 Hz, with the amplitude of the acoustical energy varying at a frequency related to the respiration rate. Similarly, cardiac contractions typically generate acoustic signals within a frequency bandwidth between 30–90 Hz with the envelope amplitude of these acoustical signals varying at a frequency related to the heart rate.

Figure 3:
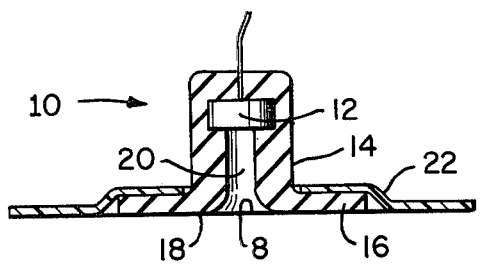
FIG. 3 is a cross-sectional view of the sensor used in the present invention.
Figure 4:
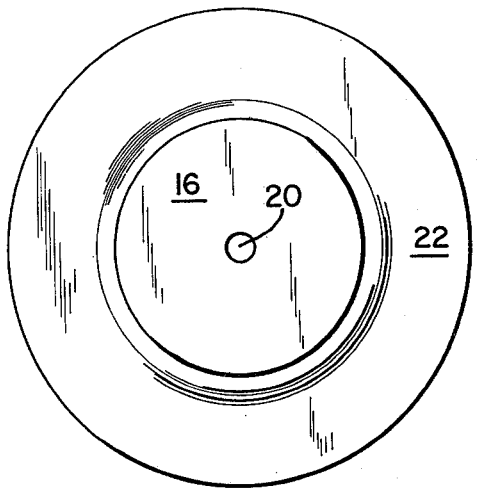
FIG. 4 is a bottom view of the sensor of FIG. 3.

As shown in FIGS. 3 and 4, the sensing means 10 may be suitably secured to the skin of a living body 8 (preferably on the chest, or on the neck) so that the sensing means will suitably detect the physiological signals of interest while at the same time be sufficiently acoustically shielded so as to minimize the amount of spurious and environmental noise detected. More specifically, sensing means 10 comprises pressure sensing unit 12 suitably mounted in the housing 14, the latter including an annular flange 16 at the contacting end 18 of the sensor (i.e., the portion of sensing means 10 actually contacting the skin of the living body 8 being monitored) and an air space or conduit 20 between unit 12 and the end 18 (1) for forming an acoustical channel so that the physiological signals of interest are conducted from the skin of the monitored body at the level 18 to the unit 12 and (2) so as to space the unit 12 from the skin to avoid contaminating the acquired signals with frictional noises which might occur from severe body motion if the unit directly contacted the skin.

Since the sensing unit 12 is spaced from the skin and the nature of the physiological signals to be detected are of a relatively weak nature, the unit 12 must be relatively sensitive at least within the bandwidth of acoustical frequencies of interest. Accordingly, the unit may be any one of several commercially available types.

The housing 18 is preferably made of a material which functions as a good acoustical shield with respect to the acoustical energy within the bandwidths of interest and yet is biologically inert so as to be non-reactive with the skin. One inexpensive and light weight material is silicone which can easily be molded over the unit 12 and formed with flange 16 and space 20 as shown in FIGS. 3 and 4. It will be obvious however, that other materials can also be used, such as neoprene.

Further, in order to provide patient comfort, the sensing means 10 preferably is small and lightweight. It is important therefore, that sensing means 10 provides an air tight acoustical seal with the skin. This is essentially provided by the flange 16 when the end 18 directly contacts the skin. In order to hold sensing means 10 in place an annular tape disk 22 having an adhesive coating, preferably of a hypoallergenic material, on one side. Disk 22 includes an inner aperture for receiving the housing 18 with an inner cross-sectional diameter smaller and an outer cross-sectional diameter larger than the cross-sectional diameter of the housing, so that the disk is secured to the flange 16, as well as the skin, when sensing means 10 is secured to the body to be monitored. It will be appreciated that all the physiological signals of interest can therefore be detected by a single sensing unit 12.

Referring to FIG. 1, the sensing means 10 therefore provides an amplitude modulated electrical signal for each physiological signal detected.

Due to the sensitivity of sensing means 10, the signal output of the sensing unit 12 not only includes the physiological signals of interest but also spurious and environmental noise which is not of interest. Through empirical studies I have discovered that with respect to the acoustical energy associated with the nonlaminar air flow through the trachea, a maximum signal-to-noise ratio typically occurs for most humans at about 400 Hz, although this can vary from person to person. It is noted that this frequency is, at least in healthy humans, independent of respiration rate as well as the age of the patient. Similarly, the acoustical energy associated with detected cardiac contractions exhibits a maximum signal-to-noise ratio at about 45 Hz. It is noted that although this frequency can also vary somewhat from person to person, the frequency itself is independent of heart rate.

In both instances, however, the amplitude of the acoustical energy is modulated at a frequency in accordance with the respiratory and heart rates, respectively. Thus, as generally shown in FIG. 1, the present invention includes means, for isolating the corresponding amplitude frequency where the maximum signal-to-noise ratio of the physiological signal is detected. In the case of respiration, the means takes the form of respiration filter 28, which is preferably a band pass filter having a center frequency or maximum transmission at about 400 Hz. Similarly, where it is desirable to detect heart rate with the sensor to the output of sensor 10 can also be connected to cardiac filter 30. The latter is preferably a band pass filter having a center frequency or maximum transmission of about 45 Hz.

Means, preferably in the form of amplitude modulation detectors 32 and 34, are provided for determining the amplitude variation or modulation of signals appearing at the outputs of the corresponding filters 28 and 30. By demodulating these signals, the output signals of detectors 32 and 34 are thus functions of the respiration and heart rates.

Figure 2:
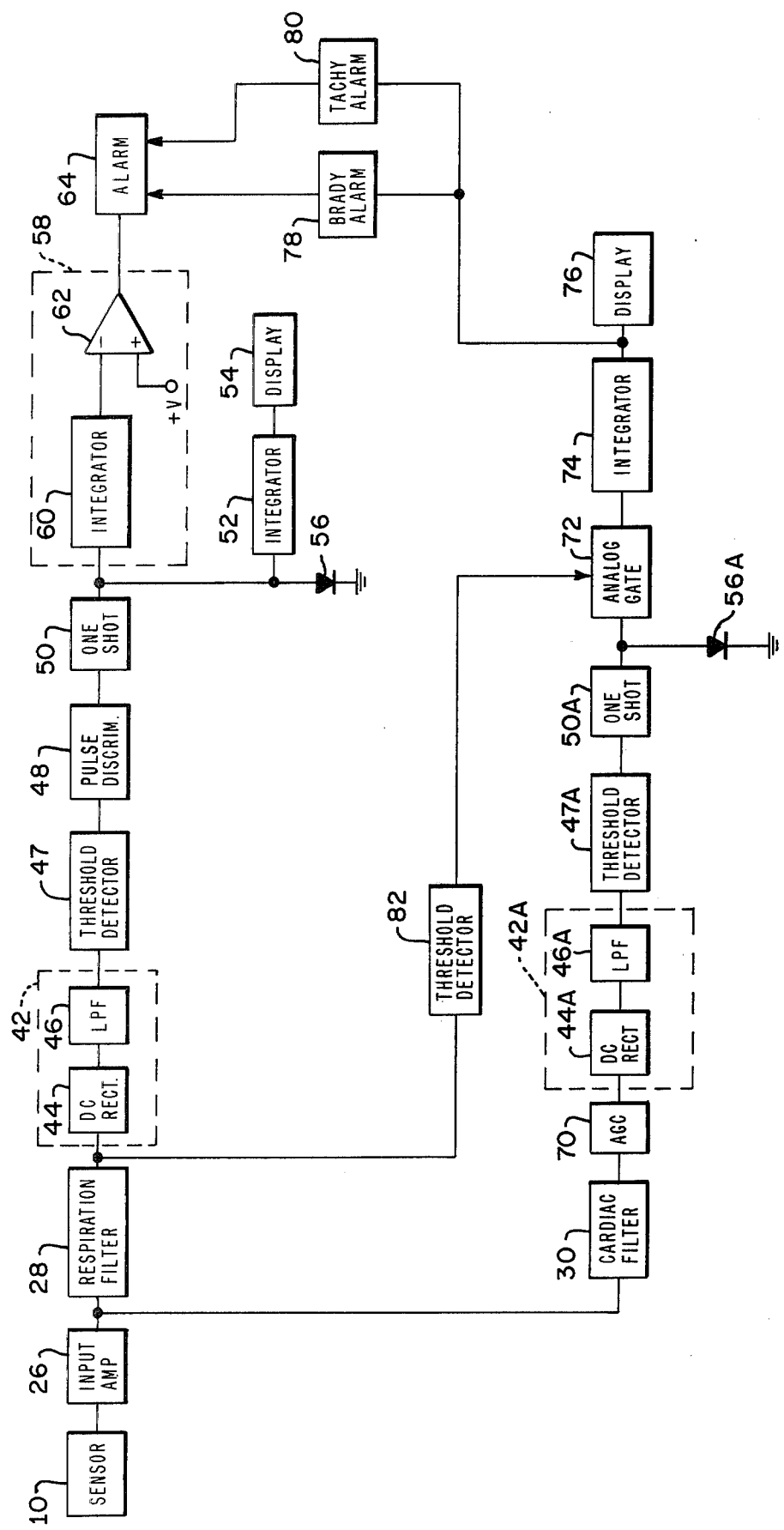
FIG. 2 is a more detailed block diagram of the embodiment of FIG. 1.

The foregoing will be more easily understood with reference to FIG. 2, where the preferred embodiment for monitoring both respiration and heart rate is shown. More specifically, sensing means 10 is connected to amplifier 26 for amplifying and shaping the signals detected. Amplifier 26 is connected to the input of both respiration filter 28 and cardiac filter 30. The latter are preferably designed to have a center frequency or maximum transmission at about 400 Hz and 45 Hz, respectively, for thr reasons previously described. The specific design of the filters may take the form of any one of several types of filters which are known in the art. The filters are preferably of the active type so as to provide a predetermined gain depending upon the relative strength of the signal. (For example, the amplitude of the heart rate signal tends to be greater than the amplitude of the respiration signal). Each filter may, for example, be a "biquadratic" filter with the center frequency of filter 28 being preferably at about 400 Hz and "skirts" preferably sloping at about 48 dB/octave; and the center frequency of the filter 30 preferably at about 45 Hz and skirts sloping at about 48 dB/octave. Each filter is designed to have a Q from between about 10 and 100, with 10 being preferred. Such biquadratic filters are well known in the art and are shown for example, in the *Motorola Data Book*, Scientific Data Library, Vol. 6, Series B, Chapter 3, P. 3-165, FIG. 11, Published by Motorola, and the General Instrument Corporation Data Catalogue, *Microelectronics*, 1977, P. 7B-2. It will be obvious however that other equivalent filters can be used such as state variable filters, or a series of high and low Butterworth filters suitably ganged together. The output of the respiration filter 28 is connected to means 42 for demodulating the output of the signal so as to provide a signal representative of the envelope of the signal output of the filter. This means is shown as including a D.C. rectifier 44, preferably a full wave rectifier, connected to receive the output of filter 28 and rectify the same. The rectified signal is then, in turn, applied to low pass filter 46. The latter is preferably designed to pass the envelope frequencies within the bandwidth of interest. Thus, filter 46 should pass those frequencies below about 10 Hz although this can vary as described.

The output of low pass filter 46 is then applied to threshold detector 47. The latter may be in the form of a comparator whose threshold is set above circuitry noise. More specifically, as well known in the art, a comparator generally is provided with a positive and a negative input terminal. Where the voltage level at the positive input is below the voltage level at the negative input, the output of the comparator will be zero. Should, however, the positive input level exceed that of the negative input level, the output is of a predetermined voltage level. Thus, with the threshold level applied to the negative input set above circuiting noise, the output of the comparator will be a train of pulses, each pulse having a duration which is a function of respiration duration, i.e., the time of each breath taken by the subject being monitored. In addition to circuitry noise, the comparator will also eliminate some motion and ambient noise so as to reduce the number of false signals.

It is noted that although not shown, automatic variable threshold correction to the comparator can be provided, by any one of several well known techniques. For example, a control signal for such correction can be devised either from the output of the low pass filter 46 or from the output of an integrator having its input suitably connected to the output of the respiration filter 28. It will be appreciated that other types of devices can be used for the threshold detector 47. For example, a window detector can be used in which only those signals within a predetermined range of amplitudes are detected. One arrangement of a window detector includes two comparators in which the input signal is applied (1) to the positive input of one comparator having its negative input set at a lower threshold level (the lower limit), and (2) the negative input of the other comparator having its positive input set at the upper threshold level. The output of the two comparators are connected to the two inputs of an AND gate. The output of the latter will be of a positive voltage so long as the voltage input to the two comparators is between the two threshold levels set. However, should the signal drop below the lower threshold level or rise above the upper threshold level the output of the AND gate drops to substantially system ground level. With this arrangement not only would low amplitude noise (below the lower threshold level limit) be rejected but also high amplitude noise (above the upper threshold limit), attributable to motion artifacts and the like, would also be eliminated. Other schemes can also be utilized for deriving a signal representative of the respiration rate. For example, although rectifier 44 is preferably a full wave rectifier to provide greater signal information, it may, if desired, also be a half wave rectifier. Further, the rectifier 44 can be omitted and detector 47 can take the form of an absolute value detector, the latter also being well known in the art. In any event, the output of detector 47 is series or train of pulses, the repetition rate being a function of respiration rate.

Although the arrangement thus far described is designed to eliminate noise from the signal, some noise within the amplitude range and frequency range of interest may still be present in the output of detector 47. Accordingly, means are provided for eliminating a substantial portion of this noise from the signal. In order to accomplish this, it has been determined that each breath takes a finite period of time, for humans typically greater than 300–900 millisecs, but usually not exceeding 2-3 seconds and thus each pulse at the output of detector 47 will be of a duration representative of at least that length when the pulse is in fact derived from respiration. It has also been determined that signals derived from motion artifacts are typically of a relatively shorter duration, i.e., less than 300–400 millisecs. Accordingly means are provided for discriminating between pulses of duration representative of less than a predetermined time period, e.g. 400 msec., and may also reject those representative of time durations exceeding a predetermined time period, e.g. 3 or 4 secs. More specifically, the output of the detector 47 is connected to the input of a pulse discriminator 48. Where only those pulses having a duration below a predetermined time period are rejected, the pulse discriminator may be a digital low pass filter and where those pulses having a duration above a predetermined level are also rejected the discriminator may be a digital band pass filter. Digital filters are well known in the art, and are described for example, in RCA 1975 Data Book, *SSD-203C, COSMOS IC's* P. 525, FIG. 30, and *Circuit Design Idea Handbook*, edited by William Furlow, "Pulse Width Discriminator" by Ira Spector, EDN Magazine, Cahners Books, Boston, MA. The output of the discriminator is a pulse of the same duration as any pulse provided by the detector 47 having a duration within the limits set by the discriminator and more specifically of a duration representative of each respiration cycle.

The output of discriminator 48 is applied to the one-shot multivibrator 50 which, in turn, provides a single pulse of fixed amplitude and of a predetermined duration for each pulse received at its input. Thus, each output pulse of the multivibrator has a finite amount of energy and is indicative of each respiration cycle. Where the metering of respiration rate is desired, the output of multivibrator 50 can be connected to the input of integrator 52.

The integrator, which may be in the form of an RC circuit, is adapted to provide an analog voltage output, the value of which is dependent on the rate of pulses provided by the multivibrator 50. Since each pulse contains the same amount of energy, the integrator will charge and discharge at a rate dependent on the repetition rate of the pulses from the multivibrator which in turn is a function of respiration rate. Thus, the voltage level of the output can be applied to a suitable display 54, such as a digital display, to indicate the respiration rate. Similarly, the output of multivibrator 50 can be applied to a light indicator 56 such as an LED (Light emitting diode) so that the latter is energized for each respiration cycle.

The output of multivibrator 50 is also connected so as to provide an apnea monitoring device. More specifically, the output of a multivibrator 50 is connected to the input of apnea timer 58. The latter preferably includes an integrator 60 connected to the negative input of a threshold amplifier 62. The nature of the integrator is such that it charges each time a pulse is received from the multivibrator to a value above the threshold level of the amplifier. The integrator has a discharge rate set at a predetermined level such that the output of the integrator will not fall below the threshold unless or until the time between two successive pulses exceeds some predetermined time limit, e.g. 10, 20 or 30 seconds, which may be adjustable by merely adjusting the threshold level of the amplifier or by varying the RC time constant of the integrator. The output of threshold amplifier 62 remains at a substantial zero voltage level until the output falls below the threshold level whereupon the output of the amplifier goes to some finite value. In the latter situation the output signal can be used to drive an alarm 64, which may be any type of alarm (and may incorporate telemetering techniques) which when actuated provides a visual or sonic indication that the sensor 10 no longer detects respiration. The alarm may be provided with a suitable reset mechanism, such alarms being well known, should the person monitoring wish to turn off the alarm once triggered on.

As previously described the same sensing means 10 can simultaneously also be used to monitor heart rate. More specifically, the output of amplifier 26 is also connected to the cardiac filter 30 which is in turn, preferably connected to the automatic gain controller 70. Such controllers are well known and thus controller 70 will not be described in detail. Generally, the automatic gain controller automatically senses the amplitudes of the signals associated with heart rate and compensates for variations so that relatively weak signals are made stronger and conversely relatively strong signals are made weaker. The use of controller 70 eliminates the need for adjusting the sensitivity of the instrument to the living body being monitored. The output of controller 70 is demodulated by demodulator 42A which is substantially identical to demodulator 42 and thus preferably includes DC rectifier 44A and low pass filter 46A. DC rectifier 44A and low pass filter 46A are substantially the same as the respective rectifier 44 and low pass filter 46, except that the former are designed to amplitude demodulate the acoustical energy associated with heart rate and the latter acoustical energy associated with respiration. The output of filter 46A is connected to the input of threshold detector 47A, the latter being similar to detector 47, except the threshold level of detector 47A is set above the circuit and ambient noise associated with the detection of heart rate.

The output of detector 47A is connected directly to the input of one-shot multivibrator 50A, the latter being substantially identical to multivibrator 50. The output of multivibrator 50A is connected through light-emitting diode 56a to ground.

In order to prevent the noise associated with vocal expression, i.e. speaking, crying, etc, (which may contain acoustic frequencies within the range of interest), from incorrectly being considered as part of the cardiac signal detected, the system preferably includes means for ignoring the acoustical energy associated with such vocal expression. More specifically, analog gate 72 has its input connected to receive the output of one-shot multivibrator 50A and its output connected to the input of integrator 74. Analog gates are well known in the art, and thus gate 72 will not be described in great detail. Generally, the analog gate is closed and transmits the signal at its input to its output substantially undistorted so long as no signal appears at its control terminal. If, however, a signal is provided at its control terminal, the gate acts as an open circuit between the input and output. The control terminal of the analog gate, accordingly, is connected to receive the output of threshold detector 82 which has its input connected to receive the output of respiration filter 28.

The threshold detector 82 is preferably a comparative amplifier having a relatively large DC threshold signal applied to its negative input and the output of filter 28 applied to its positive input. The DC threshold signal is selected to be well above the maximum signal levels associated with the acoustical energy related to respiration appearing at the output of filter 28. For example, a DC reference signal set 10 to 20 times above the level of typical respiration signals is satisfactory since vocal expression normally generates accoustical energy in the 400 Hz range well above such a reference signal level. Thus, normal respiration will be insufficient to generate a large enough signal to the positive input of the detector 82 as to generate a control signal to the analog gate 72. In such a situation the gate 72 will remain closed so that the output of the multivibrator 50A is transmitted through the gate to the integrator 74. If, however, the body being monitored makes some vocal expression, a relatively large acoustical signal appears at the output of the filter 28, which is greater than the threshold signal level of detector 82, so that the output of the detector goes to a positive signal so long as the large accoustical energy is present. The positive signal output of the detector 82 is applied to the control terminal of the gate so as to cause the latter to open, preventing the output of the multivibrator 50A, (which output will also contain the accoustical energy assocoated with vocal expression) from being passed to the integrator 74.

The integrator 74 is designed to charge and discharge in accordance with a predetermined time constant so that the instantaneous analog voltage signal level held in the integrator corresponds to the heart rate of the body being monitored. The integrator is preferably designed to discharge through analog gate 72 only when the latter is closed so that when the analog gate is open the integrator will not discharge holding its analog value. The instantaneous analog voltage output of integrator 72 is applied to the display 76, which may be digital or the like, to provide a visual indication of heart rate and is also preferably applied to the inputs of the alarm drives 78 and 80. Drives 78 and 80 are designed to drive alarm 64 should the monitored body experience bradycardia or tachycardia, respectively.

More specifically, alarm drives 78 and 80 are preferably threshold detectors in the form of comparative amplifiers, with the bradycardia drive 78, having a DC threshold level signal applied to its positive input and its negative input connected to receive the output from integrator 74. An output of the bradycardia alarm drive 78 will trigger alarm 64 should the analog input of integrator 64 drop below the threshold level indicating an abnormally slow heart rate. The tachycardia alarm drive 80 is preferably in the form of a comparative amplifier having a DC threshold level signal applied to its negative input and its positive input connected to receive the output from integrator 64. An output of tachycardia alarm drive 80 will trigger alarm 64 should the analog voltage output of integrator 74 exceed the threshold level setting of the amplifier indicating an abnormally fast heart rate.

In operation the sensing means 10 is applied, for example, to the thorax or neck area of the subject by placing the flange 16 against the skin 8 of the body and securing the sensing means in place with the tape disk 22. Sensing means 10 immediately will detect the acoustical energy associated with both respiration and heart rate with the signals being amplified by amplifier 26. The filter 28 will pass those frequencies normally associated with respiration while the filter 30 will simultaneously pass the accoustical signals associated with the heart beat. The gain of the output of the cardiac filter 30 will be automatically adjusted by the gain control 70. The output of the respiration filter 28 and the control 70 are demodulated by the demodulators 42 and 42A, respectively. It will be appreciated that the demodulator signals are representative of the respiration and heart rate cycles. Assuming that the subject being monitored provides no vocal expression to provide high energy signals, the demodulated signals of the output of demodulator 42 will be below the threshold level of detector 82 so as to maintain the analog gate 72 closed so as to transmit a signal therethrough. However, the output levels of demodulators 42 and 42A will be above the threshold levels of detectors 47 and 47A so that a train of pulses is provided at the output of each of the detectors, the pulse repetition rate corresponding to respiration and heart rates. In order to remove those pulses which correspond to spurious noise and motion artifacts detected within the acoustical range of interest the pulse train output of threshold detector 47 is applied to the pulse discriminator 48. The output of pulse discriminator 48 will remove substantially all the pulses provided by detector 47 contributed to by motion artifacts which will be of a duration substantially less than the duration normally associated with the respiration cycle. The output of pulse discriminator 48 is therefore applied to the one-shot multivibrator 50, while the output of threshold detector 47A is provided to the one-shot multivibrator 50A. So long as normal breathing and heart rate occur the outputs of multivibrators 50 and 50A will each provide a pulse corresponding to the respiration and heart rate cycle, respectively. In this way the integrator 52 will provide a sufficient analog voltage output to the display 54 and to the integrator 60 of the apnea timer so that the alarm 64 will not be triggered. If, however, the respiration stops for the time period set by the positive input of the comparator amplifier 62 of the timer 58, the alarm 64 will be triggered. Similarly, if the heart rate should fall below the setting of the bradycardia alarm drive 78 or should increase above the level set by the tachycardia alarm drive 80, the alarm 64 will also be triggered.

If the subject should provide some vocal expression while being monitored it will be appreciated that the output of filter 28 will provide a relatively high signal, above the threshold level of detector 82, so as to open analog gate 72, preventing the analog value of the integrator 74 from discharging and freezing display 76.

Figure 5:
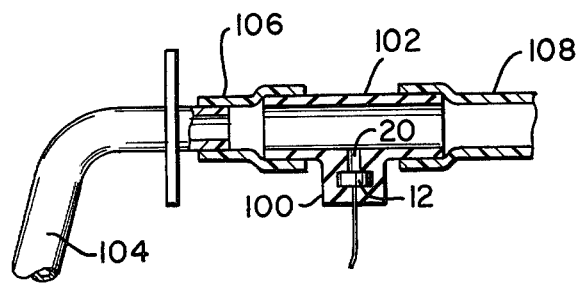
FIG. 5 is a partial fragmented view of the sensor of the FIG. 1 embodiment when used with other respiratory instruments.

It will be appreciated that in addition to the placing the sensing means 10 directly to the skin 8 of the subject, it can also be used with other respiratory devices, such as tracheostomy and endotracheal tubes. More specifically, referring to FIG. 5 the sensing unit 12 is secured within a cylindrical extension 100 which extends from a main hollow cylinder 102. The cylindrical extension 100 has its cylindrical axis substantially perpendicular to the center axis of the cylindrical tube 102. The cylindrical extension 100 is provided with the space or conduit 20 so that the space 20 extends from the sensor 20 into the hollow portion of the tube 102. The extension 100 is positioned approximately in the center between the opposite ends of the tube so that the tube 102 may be suitably attached at one end to the respiratory instrument 104 with a suitable adapter 106, and in the case where the instrument is used for ventilation, the opposite end of the tube can be attached to a suitable ventilation tube 108, which in turn is connected to a suitable ventilating device. With the arrangement of FIG. 5 the air normally associated with breathing passes through respiratory device 104, through adaptor 106, tube 102 and tube 108. It will also be appreciated that the hollow tube associated with the device 104 also acts as an acoustical conduit for the pressure waves of interest so that the sensing device 102 will detect the acoustical energy associated with respiration.

It will be appreciated therefore that the above-described invention provides several advantages over the prior art. Specifically, the device provides a relatively easy way of detecting one or more physiological signals with a single, light weight, sensor easily attached to the body being monitored without discomfort. Further, the device provides an improved monitoring device which is relatively insensitive to motion and particularly relatively insensitive to motion artifacts. Additionally, respiration can easily be monitored by detecting the flow of air through the trachea, which is one of the simplest noninvasive parameters to indicate the presence or absence of normal respiration and ventilation to the atmosphere. The device also is improved in that it can simultaneously monitor respiration as well as heart rate by using a simple and easily attached sensing means. Finally, the device is easily adapted for use with respiratory instruments, such as endotracheal and tracheostomy tubes. Since certain changes may be made in the above apparatus without departing from the scope of the invention herein involved, it is intended that all matter contained in the above description and the accompanying drawing shall be interpreted in an illustrative and not in a limiting sense.

What is claimed is:

1. A system for monitoring over relatively long periods of time, the rate of at least one physiological rhythmic function of a subject, said system comprising, in combination:

detection means for detecting acoustical energy generated by said subject within a predetermined, relatively narrow acoustical frequency band, characteristic of and unique with respect to said function, said detection means being attachable to said subject allowing the subject to move and generate motion artifacts;

generating means for generating an electrical signal representative of the acoustical energy within said frequency band and detected from the subject;

demodulating means for demodulating said electrical signal so as to produce a demodulated electrical signal and so as to detect any periodic amplitude modulation frequency of said electrical signal;

means for distinguishing between the portions of the demodulated electrical signal representative of acoustical energy detected from the subject and attributed to said function and at least some of those portions of the demodulated electrical signal representative of acoustical energy detected and attributed to said motion artifacts; and means for generating a function rate signal as a function of the portions of the demodulated electrical signal representative of the acoustical energy detected from the subject and attributed to said physiological function;

wherein the portions of the demodulated electrical signal representative of acoustical energy detected from the subject and attributed to said physiological function encompasses a band of frequencies which includes the frequency at which the optimum signal-to-noise ratio occurs in order to distinguish between those portions of the demodulated electrical signal generated by acoustical energy detected from the subject and attributed to said function at typical, normal amplitude levels and spurious electrical signals generated by acoustical energy within said band and attributed to said motion artifacts.

2. A system in accordance with claim 1, wherein said physiological function is the cardiac rate of said subject and said frequency band includes frequencies between about 30 Hz and about 90 Hz.

3. A system in accordance with claim 2, wherein said generating means includes bandpass filter means having a center frequency at about 45 Hz so as to provide said optimum signal-to-noise ratio.

4. A system in accordance with claim 1, wherein said means for distinguishing includes means for generating a pulse train in response to said demodulated signal, the repetition rate of said pulse train being representative of said periodic amplitude modulated frequency.

5. A system in accordance with claim 4, wherein said demodulating means includes means for rectifying said electrical signal so as to produce a rectified signal and means for generating said demodulated electrical signal representative of the envelope of the rectified signal, and said means for generating said pulse train includes detection means for providing an output signal so long as the amplitude of said demodulated signal exceeds some predetermined amplitude above spurious noise.

6. A system according to claim 5, wherein said detection means provides an output signal so long as the amplitude of said demodulated signal is below some second predetermined amplitude below noise associated with said motion artifacts and above the first-mentioned predetermined amplitude.

7. A system according to claim 5, wherein the pulse width of each pulse of said pulse train associated with the physiological function is within a predetermined time range, and said system further includes means for determining the repetition rate of those pulses within said time range.

8. A system according to claim 7, wherein said means for determining the repetition rate includes means for providing said function rate signal as an analog signal, the amplitude of said analog signal being a function of said repetition rate of those pulses within said time range.

9. A system according to claim 8, further including indication means for indicating when the amplitude of said analog signal drops below a first predetermined value or rises above a second predetermined value.

10. A system according to claim 9, wherein said rate of said physiological function is the cardiac rate of said subject, and the amplitude of said analog signal below said first predetermined value corresponds to a bradycardia condition and an amplitude of said analog signal above said second predetermined value corresponds to a tachycardia condition.

11. A system for monitoring over a relatively long period of time the respiration rate of a subject, said system comprising, in combination:

detection means for detecting acoustical energy generated by said subject within a predetermined, relatively narrow acoustical frequency band characteristic of and unique with respect to the respiration function of the subject, said detection means being attachable to said subject allowing the subject to move and generate motion artifacts;

generating means for generating an electrical signal representative of the acoustical energy detected from the subject within the frequency band;

demodulation means for demodulating said electrical signal so as to produce a demodulated electrical signal and so as to detect any periodic amplitude modulation frequency of the electrical signal;

means for distinguishing between those portions of the demodulated electrical signal representative of acoustical energy detected from the subject and attributed to respiration and at least some of those portions of the demodulated electrical signal representative of acoustical energy detected and attributed to said motion artifacts; and means for generating a respiration rate signal as a function of the portions of the demodulated signal representative of acoustical energy detected from the subject and attributed to respiration;

wherein the portions of the demodulated electrical signal representative of acoustical energy detected from the subject and attributed to respiration encompasses a band of frequencies which includes the frequency at which optimum signal-to-noise ratio occurs so as to easily distinguish between those portions of the demodulated electrical signal representative of acoustical energy detected from the subject and attributed to respiration at typical, normal amplitude levels and spurious electrical signals generated by acoustical energy within said band and attributed to said motion artifacts.

12. A system in accordance with claim 11, wherein said frequency band includes frequencies between about 300 Hz and about 600 Hz.

13. A system in accordance with claim 12, wherein said generating means includes bandpass filter means having a center frequency selected to provide said optimum signal-to-noise ratio.

14. A system in accordance with claim 13, wherein said center frequency is about 400 Hz.

15. A system according to claim 11, wherein said means for distinguishing between those portions of said demodulated signal includes means for generating a pulse train, the repetition rate of which is representative of said periodic amplitude modulated frequency and means for determining the repetition rate of those pulses having widths within a predetermined range of time durations.

16. A system according to claim 15, wherein said means for determining said repetition rate includes means for providing said respiration rate signal as an analog signal the amplitude of said analog signal being a function of said repetition rate of those pulses having widths within said range.

17. A system according to claim 16, further including indication means for indicating when the amplitude of said analog signal drops below a predetermined value.

18. A system according to claim 16, wherein said predetermined value corresponds to the cessation of breathing for a predetermined period of time.

19. A system according to claim 15, wherein said predetermined range of time durations is between about 300 and about 600 milliseconds.

20. A system according to claim 4, wherein the acoustical energy generated by said subject and attributed to the respiration function is generated by the nonlaminar flow of air through the trachea of said subject.

21. A system for simultaneously monitoring over a relatively long period of time the respiration rate and heart rate of a subject, said system comprising, in combination:
an acoustical detector for detecting acoustical energy generated by said subject within a first predetermined, relatively narrow acoustical frequency band characteristic and unique with respect to the respiration function of the subject and within a second predetermined relatively narrow acoustical frequency band characteristic and unique with respect to the cardio-vascular function of the subject;
first generating means for generating a first electrical signal representative of the acoustical energy detected from the subject within said first frequency band;
second generating means for generating a second electrical signal representative of the acoustical energy detected from the subject within said second frequency band;
first demodulation means for demodulating said first electrical signal so as to produce a first demodulated electrical signal and so as to detect any periodic amplitude modulation frequency of the first electrical signal as a function of the respiration rate of the respiration rate of the subject;
second demodulation means for demodulating said second electrical signal so as to produce a second demodulated electrical signal and so as to detect any periodic amplitude modulation frequency of the second electrical signal as a function of the heart rate of the subject; and
means coupled to each of the outputs of said first and second demodulator means for respectively monitoring each of said first and second demodulated signals independently of the presence of acoustical energy arising from vocal expression.

22. A system according to claim 21, further including means for selectively disabling the output of said second demodulator upon a vocal expression above a predetermined threshold.

23. A system according to claim 22, wherein said means for selectively disabling the output of said second demodulator means includes detection means for detecting signals associated with vocal expression when present with the signal associated with the cardio-vascular function and means for gating said signal associated with the cardio-vascular function so as to reject those portions of said signal associated with the cardio-vascular function which inlcudes signals associated with said vocal expression.

24. In combination with a respiratory device of the type including a tube insertable through the trachea of a subject, an improved device for monitoring the respiration rate of said subject over relatively long periods of time, said device comprising, in combination:
detection means, coupled to said tube, for detecting acoustical energy generated by said subject through said tube within a predetermined relatively narrow bandwidth characteristic of and unique with respect to the respiration function of the subject;
generating means for generating an electrical signal representative of the acoustical energy detected from the subject within the frequency bandwidth;
demodulation means for demodulating said electrical signal so as to produce a demodulated signal and so as to detect any periodic amplitude modulation frequency of the electrical signal;
means for distinguishing between those portions of the demodulated electrical signal representative of acoustical energy detected from the subject and attributed to respiration and those portions of the demodulated electrical signal representative of acoustical energy detected and attributed to motion artifacts; and
means for generating a respiration rate signal as a function of the portions of the demodulated electrical signal representative of the acoustical energy detected from the subject and attributed to the respiration rate;
wherein the portions of the demodulated electrical signal representative of acoustical energy detected from the subject and attributed to respiration encompasses a band of frequencies which includes the frequency at which the optimum signal-to-noise ratio occurs so as to easily distinguish between those portions of the demodulated electrical signal detected from the subject and attributed to respiration and spurious electrical signals generated by acoustical energy within said band and attributed to said motion artifacts.

25. In a device according to claim 24, wherein said tube is an endotracheal tube.

26. In a device according to claim 24, wherein said tube is a tracheostomy tube.

* * * * *

UNITED STATES PATENT AND TRADEMARK OFFICE
CERTIFICATE OF CORRECTION

PATENT NO. : 4306567
DATED : December 22, 1981
INVENTOR(S) : Jerome L. Krasner

It is certified that error appears in the above—identified patent and that said Letters Patent are hereby corrected as shown below:

Claim 7, column 12, line 14, "5" should be -- 6 --.

Claim 20, column 13, line 39, "4" should be -- 11 --.

Claim 23, column 14, line 23, "inlcudes" should be -- includes --.

Signed and Sealed this

Ninth Day of March 1982

[SEAL]

Attest:

GERALD J. MOSSINGHOFF

Attesting Officer

Commissioner of Patents and Trademarks